US006322774B1

(12) United States Patent
Jensen et al.

(10) Patent No.: US 6,322,774 B1
(45) Date of Patent: Nov. 27, 2001

(54) DENTAL BLEACHING COMPOSITIONS CONTAINING SUCRALOSE

(75) Inventors: Steven D. Jensen, Riverton; Dan E. Fischer, Sandy, both of UT (US)

(73) Assignee: Ultradent Products, Inc., South Jordan, UT (US)

(*) Notice: Subject to any disclaimer, the term of this patent is extended or adjusted under 35 U.S.C. 154(b) by 0 days.

(21) Appl. No.: 09/609,787

(22) Filed: Jul. 5, 2000

Related U.S. Application Data

(63) Continuation-in-part of application No. 09/468,280, filed on Dec. 20, 1999.

(51) Int. Cl.$^7$ .............................. A61K 7/16; A61K 7/20; A61K 6/00
(52) U.S. Cl. .................... 424/53; 424/49; 433/215
(58) Field of Search ........................................ 424/49–58

(56) References Cited

U.S. PATENT DOCUMENTS

| | | | |
|---|---|---|---|
| 4,140,772 | * | 2/1979 | Korenowski ................. 423/212 |
| 4,343,934 | | 8/1982 | Jenner et al. ................. 536/122 |
| 4,431,631 | * | 2/1984 | Cliffer et al. ................. 424/53 |
| 4,435,440 | | 3/1984 | Hough et al. ................. 426/658 |
| 4,495,170 | * | 1/1985 | Beyts et al. .................. 424/48 |
| 4,839,156 | * | 6/1989 | Ng et al. ..................... 424/53 |
| 4,895,721 | * | 1/1990 | Drucker ...................... 424/53 |
| 4,927,646 | * | 5/1990 | Jenner et al. ................. 426/96 |
| 4,959,225 | * | 9/1990 | Wong et al. .................. 426/3 |
| 4,971,797 | | 11/1990 | Cherukuri et al. ............. 424/440 |
| 4,980,152 | * | 12/1990 | Frazier et al. ................. 424/52 |
| 5,093,387 | | 3/1992 | Schobel et al. ............... 523/120 |
| 5,208,010 | * | 5/1993 | Thaler ........................ 424/53 |
| 5,240,697 | | 8/1993 | Norfleet et al. ............... 424/52 |
| 5,352,439 | | 10/1994 | Nofleet et al. ................ 424/52 |
| 5,374,417 | | 12/1994 | Norfleet et al. ............... 424/49 |
| 5,380,541 | * | 1/1995 | Beyts et al. .................. 424/548 |
| 5,455,285 | | 10/1995 | Carroll ....................... 523/109 |
| 5,486,350 | | 1/1996 | Norfleet et al. ............... 424/49 |
| 5,503,823 | | 4/1996 | Norfleet et al. ............... 424/52 |
| 5,505,933 | | 4/1996 | Norfleet et al. ............... 424/52 |
| 5,760,102 | | 6/1998 | Hall et al. .................... 523/120 |
| 5,849,267 | | 12/1998 | Collins et al. ................ 424/49 |
| 5,851,512 | * | 12/1998 | Fischer ....................... 424/49 |
| 5,967,155 | | 10/1999 | Marcon ...................... 132/321 |

FOREIGN PATENT DOCUMENTS 0 030 804    6/1981  (EP) .

OTHER PUBLICATIONS

Rembrandt Xtra–Comfort Non–Sensitizing Bleaching Gel Extra Strength Glycerine Urea Peroxide Potassium Nitrate Alumina Sodium Nitrate Dihydrate Perosil Flavor Garbopol 940 Trolamine Pepsin, Sep. 25, 1998.*
Registered Trademark 2270880 Den–Mat Corporation, Aug. 17, 1999.*
Dentistry Today "Buyers' Guide To Whitening Systems", Dec. 1997.*

* cited by examiner

*Primary Examiner*—Shep K. Rose
(74) *Attorney, Agent, or Firm*—Workman, Nydegger & Seeley

(57) ABSTRACT

Dental bleaching compositions that include sucralose as a non-nutritive sweetener. The bleaching agent is dispersed within a carrier, which is optimally sticky and viscous, such as a mixture of a liquid or solvent carrier and a tackifying agent. Propylene glycol and/or glycerin are especially useful liquid or solvent carriers. Flavorants may be added to enhance the taste of the dental compositions, since they will be used within a person's mouth. For best results, a flexible, thin-walled, comfortable-fitting, custom dental tray is used with the dental bleaching compositions. The dental compositions are preferably sufficiently sticky and viscous so as to adhere and retain a dental tray against a person's teeth which is designed so as to not exert significant mechanical pressure onto the person's teeth.

30 Claims, No Drawings

DENTAL BLEACHING COMPOSITIONS CONTAINING SUCRALOSE

RELATED APPLICATION

This application is a continuation-in-part of U.S. application Ser. No. 09/468,280, filed Dec. 20, 1999, in the names of Steven D. Jensen and Dan E. Fischer, D D S. For purposes of disclosure, the foregoing application is incorporated herein by specific reference.

BACKGROUND OF THE INVENTION

1. The Field of the Invention

The present invention relates to dental bleaching compositions and methods for bleaching teeth surfaces. More particularly, the present invention is directed to dental bleaching compositions which incorporate a non-nutritive sweetener, sucralose, which has been found to be stable in the presence of bleaching agents.

2. The Relevant Technology

Since its introduction in early 1989, there has been significant interest among the dental profession and the general public for home-use tooth bleaching products and methods. In its simplest form, home bleaching products typically include a dental bleaching composition having a form of hydrogen peroxide as the active bleaching agent. Some compositions are in the form of toothpastes that are simply brushed onto the teeth during a person's daily dental hygiene routine. Other, more specialized bleaching compositions are adapted for extended contact with the teeth to be bleached, such as by means of a dental tray, or for rapid whitening with the use of chemical accelerators or lasers.

As a general rule, whitening toothpastes have largely been ineffective in whitening teeth due to their relatively low potency or concentration of active bleaching agent coupled with the short duration of contact of such formulations with a person's teeth. Because of the manner in which toothpastes are manufactured, shipped, stored and sold, toothpastes are largely incapable of incorporating higher concentrations of active bleaching agents that remain stable over the intended manufacturing and storage life of the toothpaste prior to use. Many abrasives, particularly those which release metal ions, are known to trigger the decomposition of peroxide bleaching agents. Moreover, it is well-known that people typically brush for 60 seconds or less, thus further reducing the effectiveness of the already low concentration bleaching agent within over-the-counter toothpastes. In view of the foregoing, bleaching compositions having increased bleaching activity coupled with methods that maintain such dental compositions in contact with the teeth for longer periods of time are necessary to effect a noticeable bleaching effect in most people. Typical dental bleaching compositions include from 5–20% by weight of carbamide peroxide ($CO(NH_2)_2 \cdot H_2O_2$), which is a complex of urea and hydrogen peroxide.

Such dental bleaching compositions are typically applied to a person's teeth using a dental tray configured so as to retain the dental composition against the person's teeth. A self-sealing dental "splint" that can be used with more fluid and less sticky dental bleaching compositions are disclosed in U.S. Pat. No. Re. 34,196 to Munro. Munro recommends the use of Proxigel®, manufactured according to U.S. Pat. No. 3,657,413 to Rosenthal, which at the time contained only 0.6% carboxypolymethylene as a thickening agent, or a mixture of Proxigel® and Peroxyl® gel, which is an even more fluid bleaching composition than Proxigel®. The Munro dental tray is especially suitable for use with such highly fluid dental compositions since it is made from a rigid plastic material and configured so as to form a fluid-tight seal against the person's gums. Such trays, however, are not always comfortable for the user, particularly when the dental tray is held in place over long periods of time within a person's mouth.

Flexible, more comfortable-fitting dental trays that are preferably used in combination with more sticky and viscous dental bleaching compositions are disclosed in U.S. Pat. Nos. 5,098,303 and 5,234,342, both to Fischer. Such dental trays, while being more flexible and generally thinner-walled compared to prior dental trays, are preferably trimmed in a preferred embodiment so as to terminate below the gingival margin and then scalloped up and around the interdental papilla. This provides maximum bleaching of the entire surface of the person's teeth while minimizing or eliminating actual contact with the person's gums, including the interdental papilla, thus providing minimum discomfort. Further enhancement of bleaching is provides by optionally building "reservoirs" into the dental trays so as to allow for increased loading of bleaching composition within the dental tray that can contact the teeth.

One problem with dental bleaching compositions is that patients sometimes fail to use the compositions for adequate time periods due to the bitter or otherwise unpleasant taste of the dental bleaching agent. Attempts to camouflage the bitter taste have involved the use of a variety of sweeteners and other flavorants.

Nutritive sweeteners, which include sugars such as sucrose, fructose, or mannose, or sugar derivatives such as sorbitol, mannitol, and xylitol, are unfortunately not sweet enough to disguise the bitter taste. Even when added in large quantities, such sugars still cannot render compositions containing bleaching agents such as peroxides and perborates sufficiently palatable. Additionally, nutritive sweeteners such as sucrose and other sugars tend to promote tooth decay.

Non-nutritive sweeteners, which are sweeteners without caloric value, have also been utilized in dentifrices. An example of a non-nutritive sweetener is aspartame. Unfortunately, aspartame has been found to be unstable in the presence of appreciable concentrations of a bleaching agent. A non-nutritive sweetener that is more stable in the presence of bleaching agents is sodium saccharine. Sodium saccharine, however, has shown carcinogenic possibilities in some studies. As a result, sodium saccharine is only recommended for use by diabetics. Additionally, sodium saccharine itself is known to cause an undesirable bitter after taste, which may compromise its usefulness in disguising the bitter taste of bleaching agents.

From the foregoing, it will be appreciated that what is needed in the art are improved compositions and methods for manufacturing suitable dental bleaching compositions that disguised the bitter taste of bleaching agents, remained stable in the presence of such bleaching agents, and were not carcinogenic.

Additionally, it would be a significant advancement in the art to provide dental bleaching compositions having a stable sweetener that adequately disguised the bitter taste of bleaching agents which also had sufficient stickiness and viscosity so as to enable such compositions to adhere and retain a comfortable-fitting dental tray in place for the duration of a desired treatment regimen.

Such dental bleaching compositions of improved taste and less bitterness, as well as methods for their manufacture and use, are disclosed and claimed herein.

SUMMARY AND OBJECTS OF THE INVENTION

The present invention is directed to dental bleaching compositions used to treat tooth surfaces containing the non-nutritive sweetener sucralose. Sucralose and a bleaching agent are mixed with a carrier which enables the bleaching agent to contact and bleach teeth. Sucralose is many, many times sweeter than sugar and is also stable in the presence of bleaching agents so that it is able to effectively disguise the bitter taste of such agents over time. It also leaves not bitter after taste. This improved taste encourages patients to complete a prescribed bleaching regime and achieve the desired results.

The sucralose and bleaching agent are preferably dispersed within a sticky carrier. However, the sucralose and bleaching agent may also be dispersed within a carrier which is a liquid such as a liquid polyol or water. The sticky carrier may include other gelling agents such as finely divided gel-forming metal oxides and/or organic thickeners known in the art.

Because the dental bleaching compositions according to the present invention are preferably sticky and viscous, they are especially suitable for use in combination with a custom dental tray that is designed so as to not exert significant mechanical pressure onto a person's teeth. The elimination or substantial reduction of mechanical pressures that are exerted onto a person's teeth during bleaching greatly increases the comfort experienced by the user. The inventive dental bleaching compositions are preferably formulated so as to a have a stickiness and viscosity that causes the bleaching compositions to adhere and retain a flexible, thin-walled dental tray against a person's teeth for as long as needed to carry out the desired bleaching process, such as the type of dental tray disclosed in U.S. Pat. Nos. 5,098,303 and 5,234,342, both to Fischer. For purposes of disclosing flexible, thin-walled, comfortable-fitting dental trays suitable for bleaching a person's teeth, the foregoing patents are incorporated herein by specific reference.

The inventive bleaching compositions may also include other adjustments and active ingredients such as flavorants, desensitizing agents (e.g., $KNO_3$), anticariogenic agents (e.g., fluoride compounds), antimicrobial agents (e.g., antibiotics), stabilizing agents (e.g., EDTA), and the like. The carrier is preferably substantially free of abrasives, particularly those that cause bleaching agents to be unstable.

In order to carry out a desired bleaching process, the bleaching compositions of the present invention may be placed against a person's teeth for as little as 10 minutes or for as long as 8 hours or more, depending on the potency of the bleaching composition and the desired level of bleaching. Preferably, the bleaching compositions will be placed in contact with a person's teeth for at least about 30 minutes, more preferably for at least about 1 hour, and most preferably for at least about 2 hours. Depending on the desired treatment regimen, the dental bleaching compositions according to the present invention can vary in potency and stickiness in order to optimize the performance of the bleaching composition for a given treatment regimen.

It is, therefore, an object of the present invention to provide improved compositions and methods for manufacturing suitable dental bleaching compositions that include sucralose.

Another important object of the present invention is to provide dental bleaching compositions containing sucralose which also have sufficient stickiness and viscosity so as to enable such compositions to adhere and retain a suitable dental tray in place for the duration of a desired treatment regimen.

Yet another significant object of the present invention is to provide sucralose containing dental bleaching compositions which are sufficiently stable so as to be stored and then used as desired to complete a bleaching regime such that the teeth are whitened as desired.

These and other objects and features of the present invention will become more fully apparent from the description which follows, or may be learned by the practice of the invention.

DETAILED DESCRIPTION OF THE PREFERRED EMBODIMENTS

As summarized above, the present invention is generally related to dental bleaching compositions containing sucralose, a chlorinated sucrose derivative with enhanced sweetness. More proper chemical names for "sucralose" include: 1,6-dichloro-1,6-dideoxy-β-D-fructo-furanosyl-4-chloro-4-deoxy-α-D-galactopyranoside; 4,1', 6'-trichloro-4, 1', 6'-trideoxy-galacto-sucrose; 1',4,6'-trichloro-galactosucrose; and TGS. Sucralose has the general formula $C_{12}H_{19}Cl_3O_8$ and a molecular weight of 397.64. References which disclose methods for preparing sucralose include European Pat. Application 0 030 804 to Tate et al. and U.S. Pat. No. 4,343,934 to Jenner et al. U.S. Pat. No. 4,435,440 to Hough et al. describes the usefulness of sucralose as a sweetener. These references are hereby incorporated by reference.

Sucralose is non-nutritive so it has none of the disadvantages associated with nutritive sweeteners e.g., promoting tooth decay. However, it tastes very much like sugar while being approximately 600 times sweeter than sugar. Because sucralose is so sweet tasting, even a small amount of sucralose is sufficient to disguise the bitter taste of the bleaching agent. Additionally, sucralose has been found to be surprisingly stable for extended periods of time when mixed with a bleaching agent. Sucralose, unlike sodium saccharine, does not itself leave a bitter after taste. Nor is it suspected of being a carcinogen. Hence, the inventive bleaching compositions of the present invention are better tasting, with stable taste properties over time, compared to compositions that use, e.g., aspartame, and safer to use, compared to compositions that use, e.g., sodium saccharine.

Dental bleaching compositions containing sucralose within the scope of the present invention encompass a wide variety of compositions suitable for bleaching teeth. The dental bleaching compositions essentially include a dental bleaching agent and sucralose dispersed in a carrier. The carrier may be any suitable fluid such as a liquid or a gel.

The dental bleaching compositions are preferably those which are useful use with flexible, thin-walled, comfortable fitting dental trays designed so as to not exert significant mechanical pressure onto a person's teeth. Dental bleaching compositions intended for use with such dental trays typically utilize a sticky carrier formed from a fluid and a thickener. The sticky carrier accordingly often comprises finely divided silica, such as silica fume, dispersed in a liquid, such as a polyol. Examples of suitable polyols include propylene glycol, glycerin, polypropylene glycols, sorbitol, polyethylene glycols and the like. The polyethylene glycols and the polypropylene glycols preferably have low molecular weights. While the carrier preferably includes thickeners, the carrier may also be only a liquid such as water or any of the liquid polyols without any thickeners.

Other thickening, gelling or tackifying agents may be used in addition to, or instead of, fumed silica, such as finely divided alumina, titanium dioxide, zinc oxide or other insoluble particulates that are capable of forming a gel when mixed with propylene glycol, glycerin and the like. In addition to finely divided inorganic particulate tackifying agents, organic tackifying agents known in the art can be added in order to adjust the viscosity and stickiness of the composition. Natural or synthetic polymers such as natural gums, proteins, cellulosic ethers, carboxypolymethylene, high molecular weight polyols, or other gel-forming admixtures, can be used. Carbopol NF 974 is the preferred carboxypolymethylene. Examples of natural polymers include xanthan gum, guar gum, gum arabic, gum tragacanth, gum karaya, starches, cellulosic ethers, proteins, and the like. Other examples of organic tackifying agents include high molecular weight polyethylene glycol, high molecular weight polypropylene glycols, high molecular weight polyacrylic acids and high molecular weight polyethylene oxide. A useful synthetic tackifying agent is Pluronic®.

The dental bleaching agents may be any material capable of whitening teeth. Examples of suitable dental bleaching agents include aqueous hydrogen peroxide, carbamide peroxide, perborate-based bleaching agent such as sodium perborate monohydrate ($NaBO_3 \cdot H_2O$) and sodium percarbonate.

Colorants and other visual enhancing agents can be added as desired in order to yield a visually desirable dental bleaching composition. Other adjuvents and additives can also be added in minor amounts as needed to impart a desired property. For example, flavorants can be added as desired to yield bleaching compositions having a particular taste. Examples of such flavors include mint, spearmint, wintergreen, watermelon, banana, root beer, raspberry, peach, etc. Flavorants may be included in an amount in a range from about 0.1% to about 10% by weight of the dental bleaching composition.

In order to reduce tooth sensitivity, desensitizing agents may be used, an example of which is potassium nitrate ($KNO_3$). The desensitizing agent is preferably included in an amount in a range from about 0.01% to about 5%, more preferably in a range from about 0.1% to about 2% by weight of the composition.

The bleaching compositions may also include one or more anticariogenic agents, such as fluoride salts or other sources of available fluoride ions. Antimicrobial agents such as antibiotics may also be included if desired. Stabilizing agents such as ion scavengers (e.g., EDTA and salts thereof) may be employed to increase stability of the bleaching agents.

The dental bleaching agent may be included in an amount in a wide range from about 5% to about 85% by weight of the dental bleaching composition. The dental bleaching agent is preferably in a range from about 5% to about 50% by weight, more preferably in a range from about 10% to about 40% by weight of the dental bleaching composition, even more preferably in a range from about 12% to about 35% by weight of the composition, and most preferably in a range from about 15% to about 30% by weight. The content of the bleaching agent in the dental bleaching composition may be varied depending on factors such as the location of use and patient sensitivity. For example, bleaching kits used at home typically have lower concentrations of dental bleaching agents than do kits intended for use only in a dental office.

The amount of the liquid or solvent portion of the carrier in the dental bleaching composition may range from about 1% to about 95% by weight of the dental bleaching composition. The carrier is preferably in a range from about 15% to about 90% by weight, more preferably in a range from about 30% to about 80% by weight of the dental bleaching composition and is most preferably in a range from about 45% to about 75% by weight. A presently preferred liquid carrier is a polyol, such as propylene glycol.

The fumed silica or similar finely divided particle capable of forming a sticky and viscous carrier when mixed with glycerin, including fumed silica or other finely divided particles blended with optional organic thickeners, may be included in an amount in a range from about 0.5% to about 50% by weight of the dental bleaching composition. The fumed silica is preferably included in a range from about 1% to about 40% by weight of the dental bleaching composition, more preferably in a range from about 5% to about 35% by weight, and most preferably in a range from about 10% to about 30% by weight of the dental bleaching composition. Fumed silica, precipitated silica and other appropriate finely divided particles that may be used to form a viscous and sticky carrier when mixed with one or more appropriate polyols will typically have a particle size from about 0.001 micron to about 1 micron. An example of a suitable silica fume that may be used to yield sticky and viscous dental bleaching compositions when mixed with a polyol is Aerosil 200, which is manufactured by Degussa of Germany.

The organic polymer thickening agents may be included in an amount in a range from about 0.5% to about 50% by weight of the composition, preferably in a range from about 2% to about 25%, and most preferably in a range from about 3% to about 20% by weight of the dental composition.

Because preferred dental bleaching compositions according to the invention are intended for use with a dental tray, such that they will not be used as a toothpaste for daily brushing regimens, they will preferably not include an abrasive. Some abrasives may actually inhibit bleaching and also cause premature decomposition of the bleaching agent. Abrasives that release metal ions are particularly prone to cause decomposition of bleaching agents, while non-metal releasing particulates such as silica fume will not. On the other hand, extremely finely divided silica fume particles, e.g., those smaller than about 1 micron, are so small that they import little or no abrasive activity in any event.

The sucralose may be added in any suitable amount to disguise the bitter taste of the bleaching agent. When larger concentrations of dental bleaching agents are included then the concentration of the sucralose is also advantageously increased. The sucralose is preferably present in a range from about 0.01% to about 15% by weight of the dental bleaching composition, more preferably from about 0.1% to 10% by weight and most preferably from about 0.2% to about 5% by weight.

The stability of the sucralose is generally sufficient such that dental bleaching compositions can be stored for long periods and used while maintaining sufficient sweetness of the sucralose so as to mask the bitter taste of the bleaching agent. For example, a dental bleaching composition containing sucralose which is formed in accordance with the above discussed ranges is likely after 1 year to still have the same amount of sucralose as it contained when originally manufactured. In any event, the sucralose content would be expected after 1 year to be at least 85% of the amount contained in the composition after initially being formed. Similarly, such a dental bleaching composition would be expected after about 4 to 6 months to have at least 90% of the sucralose that it had when originally manufactured.

While the sucralose content remains stable, some compositions may maintain a greater bleaching efficacy for a longer period of time depending on several factors. One factor which influences the stability of the bleaching agent is the pH of the composition. Higher pH levels tend to decrease the stability of the bleaching agent in the composition. Accordingly, the composition is preferably constituted such that the pH is approximately neutral, or even slightly acid. Another factor which influences the stability of the bleaching agent in the dental bleaching compositions is the amount of the dental bleaching agent in the composition. Accordingly, compositions with high concentrations of dental bleaching agents may not have as long of a shelf life as those with lower concentrations. The type of bleaching agent utilized may also influence the shelf life stability. Carbamide peroxide is preferred for optimal shelf life stability as it is more stable than aqueous hydrogen peroxide. Refrigeration may be advantageously used to increase the shelf life and inhibit degradation of the bleaching agent.

In any event, the particular shelf life of the compositions is not limited by the stability of the sucralose. The stability of the sucralose is such that the compositions of the present invention have adequate shelf life stability to enable a dentist to store a dental bleaching composition and to enable a patient to use the composition to complete a bleaching regime with the desired sweet taste.

Although the dental bleaching compositions are not limited to the particular method or apparatus by which they are applied to a person's teeth, a preferred method for applying the dental bleaching compositions involves the use of a dental tray. A dental tray shields the composition from being rubbed off or diluted by saliva so that it can remain against the person's teeth during the desired treatment regimen. Virtually any dental tray known in the art could be used in applying the inventive bleaching compositions disclosed herein.

In a preferred embodiment, flexible, comfortable-fitting, thin-walled dental trays that are designed so as to not exert significant mechanical pressure are used to apply the inventive dental bleaching compositions disclosed herein. The dental bleaching compositions are preferably sufficiently sticky and viscous so as to adhere and retain such dental trays in place for the duration of the desired treatment time. The dental trays may optionally be formed so as to include reservoirs in order to provide additional dental bleaching composition to one or more teeth of a dental arch needing more whitening than others, or to selected parts of a tooth needing more whitening than other parts. The dental trays are preferably trimmed to below the gingival margin and also scalloped up and around the interdental papilla. As stated above, preferred dental trays are manufactured according to U.S. Pat. Nos. 5,098,303 and 5,234,342 to Fischer, which have been previously incorporated by reference.

In order to carry out a desired bleaching process, the bleaching compositions of the present invention can be placed against a person's teeth for as little as 10 minutes and for as long as 8 hours or more, depending on the potency of the bleaching composition and the desired level of bleaching. Preferably, the bleaching compositions will be placed over a person's teeth for at least about 30 minutes, more preferably for at least about 1 hour, and most preferably for at least about 2 hours. Depending on the desired treatment regimen, the dental bleaching compositions according to the present invention can vary in potency and stickiness in order to optimize the performance of the bleaching composition for a given treatment regimen.

One currently preferred method of dispensing the bleaching agent uses a syringe. Squeezable tubes and other similar dispensing devices may also be used to dispense the bleaching agent. A syringe allows for the dispensing of a desired quantity of the dental bleaching composition, whether it be a unit dose or multiple doses. In the case of a syringe capable of providing for multiple doses of bleaching composition, graduations may be provided on the syringe to assist the user in dispensing a precise quantity of the bleaching composition each time.

The following examples set forth various exemplary dental bleaching compositions within the scope of the present invention. These examples are intended to be purely exemplary and should not be viewed as limiting the scope of the present invention.

EXAMPLE 1

A dental bleaching composition within the scope of the present invention was prepared by combining the following ingredients (in weight percent):

| | |
|---|---|
| Carbamide Peroxide | 10% |
| Disodium Edetate | 0.1% |
| Polyethylene Glycol 300 | 5.5% |
| Sucralose | 1% |
| Carbopol 974 | 6.8% |
| Sodium Hydroxide (50%) | 5.7% |
| Distilled Water | 20% |
| Glycerine | 50.4% |

EXAMPLE 2

A dental bleaching composition within the scope of the present invention was prepared by combining the following ingredients (in weight percent):

| | |
|---|---|
| Carbamide Peroxide | 20.5% |
| Disodium Edetate | 0.1% |
| Polyethylene Glycol 300 | 5.5% |
| Sucralose | 1% |
| Carbopol 974 | 6.8% |
| Sodium Hydroxide (50%) | 5.7% |
| Distilled Water | 20% |
| Glycerine | 40.4% |

The resulting dental bleaching composition contained sufficient sucralose to fully disguise the bitter taste of the bleaching agent. The sucralose content would be expected to remain essentially constant after 1 year. The resulting dental bleaching composition was sticky and viscous like the composition of Example 1 but had higher bleaching power. The dental bleaching composition was able to adhere and retain a dental tray in place against a person's teeth. The dental bleaching composition was useful in bleaching the person's teeth.

EXAMPLE 3

A dental bleaching composition within the scope of the present invention is made according to the procedure of Example 1, except that the ingredients are combined in the following amounts (in weight percent):

| | |
|---|---|
| Carbamide Peroxide | 30.5% |
| Disodium Edetate | 0.1% |
| Polyethylene Glycol 300 | 5.5% |
| Sucralose | 1% |
| Carbopol 974 | 6.8% |
| Sodium Hydroxide (50%) | 5.7% |
| Distilled Water | 20% |
| Glycerine | 20.4% |

The resulting dental bleaching composition contains sufficient sucralose to fully disguise the bitter taste of the bleaching agent. The sucralose content remains essentially constant after 1 year. The resulting dental bleaching composition is sticky and viscous like the composition of Example 1 but has higher bleaching power. The dental bleaching composition is able to adhere and retain a dental tray in place against a person's teeth. The dental bleaching composition is useful in bleaching the person's teeth.

EXAMPLE 4

A dental bleaching composition within the scope of the present invention is made according to the procedure of Example 1, except that the ingredients are combined in the following amounts (in weight percent):

| | |
|---|---|
| Carbamide Peroxide | 10.5% |
| Disodium Edetate | 0.3% |
| Sucralose | 1% |
| Carbopol 974 | 6.8% |
| Sodium Hydroxide (50%) | 5.7% |
| Distilled Water | 10% |
| Propylene Glycol | 65.7% |

The resulting dental bleaching composition contains sufficient sucralose to fully disguise the bitter taste of the bleaching agent. The sucralose content remains essentially constant after 1 year. The resulting dental bleaching composition is very sticky and viscous like the composition of Example 1 and has the same bleaching power. The dental bleaching composition is able to adhere and retain a dental tray in place against a person's teeth. The dental bleaching composition is useful in bleaching the person's teeth.

EXAMPLE 5

A dental bleaching composition within the scope of the present invention is made according to the procedure of Example 1, except that the ingredients are combined in the following amounts (in weight percent):

| | |
|---|---|
| Carbamide Peroxide | 25.5% |
| Disodium Edetate | 0.1% |
| Propylene Glycol 8000 | 10% |
| Sucralose | 2% |
| Xanthan Gum | 1.8% |
| Distilled Water | 20% |

The resulting dental bleaching composition contains sufficient sucralose to fully disguise the bitter taste of the bleaching agent and is much sweeter than in Example 1. The sucralose content remains essentially constant after 1 year. The resulting dental bleaching composition is not very sticky but is relatively viscous. The bleaching composition has a higher bleaching power than in Example 1. The dental bleaching composition is able to adhere and retain a dental tray in place against a person's teeth. The dental bleaching composition is useful in bleaching the person's teeth.

EXAMPLE 6

A dental bleaching composition within the scope of the present invention is made according to the procedure of Example 1, except that the ingredients are combined in the following amounts (in weight percent):

| | |
|---|---|
| Carbamide Peroxide | 10.5% |
| Disodium Edetate | 0.1% |
| Polyethylene Glycol 300 | 5.5% |
| Sucralose | 2% |
| Carbopol 974 | 6.8% |
| Sodium Hydroxide (50%) | 5.7% |
| Distilled Water | 20% |
| Glycerine | 49.4% |

The resulting dental bleaching composition contains sufficient sucralose to fully disguise the bitter taste of the bleaching agent and is much sweeter than in Example 1. The sucralose content remains essentially constant after 1 year. The resulting dental bleaching composition is sticky and viscous like the composition of Example 1 and has the same bleaching power. The dental bleaching composition is able to adhere and retain a dental tray in place against a person's teeth. The dental bleaching composition is useful in bleaching the person's teeth.

EXAMPLE 7

A dental bleaching composition within the scope of the present invention is made according to the procedure of Example 1, except that the ingredients are combined in the following amounts (in weight percent):

| | |
|---|---|
| Aqueous Hydrogen Peroxide (30%) | 22.5% |
| Disodium Edetate | 0.1% |
| Polyethylene Glycol 300 | 5.5% |
| Sucralose | 1% |
| Carbopol 974 | 6.8% |
| Sodium Hydroxide (50%) | 5.7% |
| Glycerine | 58.4% |

The resulting dental bleaching composition contains sufficient sucralose to fully disguise the bitter taste of the bleaching agent. The sucralose content remains essentially constant after 1 year. The resulting dental bleaching composition is sticky and viscous like the composition of Example 1 and has the same bleaching power. The dental bleaching composition is able to adhere and retain a dental tray in place against a person's teeth. The dental bleaching composition is useful in bleaching the person's teeth.

EXAMPLE 8

To any of the foregoing compositions is added 0.5% by weight of potassium nitrate as a desensitizing agent.

EXAMPLE 9

To any of the foregoing compositions is added a fluoride salt.

EXAMPLE 10

To any of the foregoing compositions is added an antimicrobial agent.

From the foregoing, it will be appreciated the present invention provides improved compositions and methods for manufacturing suitable dental bleaching compositions that include sucralose.

Additionally, it will be appreciated that the present invention further provides dental bleaching compositions containing sucralose which also have sufficient stickiness and viscosity so as to enable such compositions to adhere and retain a suitable dental tray in place for the duration of a desired treatment regimen.

It will be further appreciated that the present invention provides sucralose containing dental bleaching compositions which are sufficiently stable so as to maintain the desired bleaching activity until bleaching of the teeth is desired.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dental bleaching composition comprising:
   at least one dental bleaching agent in an amount in a range from about 5% to about 85% by weight of the dental bleaching composition;
   a non-nutritive sweetening agent consisting essentially of sucralose and included in an amount so as to substantially disguise any bitter taste associated with the dental bleaching agent; and
   a carrier comprising a liquid or gel,
   wherein the dental bleaching composition is substantially free of other non-nutritive sweetening agents besides sucralose.

2. A dental bleaching composition as defined in claim 1, wherein the sucralose is included in an amount of about 0.01% to about 15% by weight of the dental bleaching composition.

3. A dental bleaching composition as defined in claim 1, wherein the dental bleaching composition has a stickiness and viscosity so that it is able to adhere and retain against a person's teeth a dental tray that is designed so as to not exert significant mechanical pressure onto the person's teeth and gums.

4. A dental bleaching composition as defined in claim 1, wherein the carrier comprises at least one polyol.

5. A dental bleaching composition as defined in claim 4, wherein the polyol is included in a range of about 15% to about 90% by weight of the dental bleaching composition.

6. A dental bleaching composition as defined in claim 4, wherein the polyol comprises at least one of propylene glycol, glycerin, polypropylene glycol, sorbitol, or polyethylene glycol.

7. A dental bleaching composition as defined in claim 4, wherein the carrier comprises at least one tackifying agent.

8. A dental bleaching composition as defined in claim 7, wherein the tackifying agent includes finely divided fumed silica in an amount in a range from about 0.5% to about 50% by weight of the dental bleaching composition.

9. A dental bleaching composition as defined in claim 7, wherein the tackifying agent includes at least one organic polymer thickening agent included in an amount of about 0.5% to about 50% by weight of the dental bleaching composition.

10. A dental bleaching composition as defined in claim 9, wherein the organic polymer thickening agent includes at least one of a natural gum, a protein, a cellulosic ether, carboxypolymethylene, a high molecular weight polyol, or pluronic.

11. A dental bleaching composition as defined in claim 1, wherein the carrier is substantially free of abrasives.

12. A dental bleaching composition as defined in claim 1, further including at least one of a desensitizing agent, an anticariogenic agent, or an antimicrobial agent.

13. A dental bleaching composition as defined in claim 1, wherein the dental bleaching agent includes at least one of hydrogen peroxide, carbamide peroxide, sodium perborate monohydrate, or sodium percarbonate.

14. A dental bleaching composition as defined in claim 1, wherein the dental bleaching agent is included in an amount of at least about 10% by weight of the dental bleaching composition.

15. A dental bleaching composition as defined in claim 1, wherein the dental bleaching agent is included in an amount of at least about 15% weight of the dental bleaching composition.

16. A dental bleaching composition as defined in claim 1, wherein the dental bleaching further includes potassium nitrate in an amount effective to desensitize teeth.

17. A dental bleaching composition as defined in claim 1, wherein the dental bleaching composition has an essentially neutral pH.

18. A dental bleaching composition comprising:
   at least one dental bleaching agent in an amount in a range from about 5% to about 85% by weight of the dental bleaching composition;
   a non-nutritive sweetening agent consisting essentially of sucralose and included in an amount so as to at least partially disguise any bitter taste associated with the dental bleaching agent; and
   a carrier comprising a sticky, viscous gel that includes at least one of an organic polymer thickening agent or a finely divided particulate thickening agent,
   wherein the dental bleaching composition (1) is substantially free of abrasives and (2) has a stickiness and viscosity so that it is able to adhere and retain against a person's teeth a dental tray that is designed so as to not exert significant mechanical pressure onto the person's teeth and gums.

19. A dental bleaching composition as defined in claim 18, wherein the carrier comprises at least one polyol.

20. A dental bleaching composition as defined in claim 18, wherein the thickening agent includes at least one of a natural gum, a protein, a cellulosic ether, carboxypolymethylene, a high molecular weight polyol, pluronic, or fumed silica.

21. A dental bleaching composition as defined in claim 18, further including at least one of a desensitizing agent, an anticariogenic agent, or an antimicrobial agent.

22. A dental bleaching composition as defined in claim 18, wherein the dental bleaching agent includes at least one of hydrogen peroxide, carbamide peroxide, sodium perborate monohydrate, or sodium percarbonate.

23. A dental bleaching composition as defined in claim 18, wherein the dental bleaching composition has a substantially neutral pH.

24. A method for bleaching a person's teeth comprising:
   providing a dental bleaching composition that comprises:
      at least one dental bleaching agent in an amount in a range from about 5% to about 85% by weight of the dental bleaching composition;

a non-nutritive sweetening agent consisting essentially of sucralose and included in an amount so as to substantially disguise any bitter taste associated with the dental bleaching agent; and a carrier comprising a liquid or gel, wherein the dental bleaching composition is substantially free of other non-nutritive sweetening agents besides sucralose, contacting the person's teeth with the dental bleaching composition for a desired treatment period.

25. A method for bleaching a person's teeth as defined in claim 24, wherein the person's teeth are contacted with the dental bleaching composition using a dental tray.

26. A method for bleaching a person's teeth as defined in claim 25, wherein the dental tray is designed so as to fit over the person's teeth without exerting significant mechanical pressure onto the person's teeth, wherein the dental bleaching composition has a stickiness such that it is able to adhere and retain the dental tray in place over the person's teeth during the desired treatment period.

27. A method for bleaching a person's teeth as defined in claim 24, wherein the carrier includes at least one of fumed silica, a natural gum, a protein, a cellulosic ether, carboxypolymethylene, or pluronic.

28. A method for bleaching a person's teeth as defined in claim 24, wherein the carrier includes a polyol.

29. A method for bleaching a person's teeth comprising:

providing a dental tray designed so as to fit over the person's teeth without exerting significant mechanical pressure onto the person's teeth;

placing within the dental tray a dental bleaching composition including:

at least one dental bleaching agent in an amount in a range from about 5% to about 85% by weight of the dental bleaching composition;

a non-nutritive sweetening agent consisting essentially of sucralose and included in an amount so as to at least partially disguise any bitter taste associated with the dental bleaching agent; and a carrier comprising a sticky, viscous gel that includes at least one of an organic polymer thickening agent or a finely divided particulate thickening agent, wherein the dental bleaching composition (1) is substantially free of abrasives and (2) has a stickiness and viscosity so that it is able to adhere and retain against a person's teeth said dental tray that is designed so as to not exert significant mechanical pressure onto the person's teeth and gums; and placing the dental tray containing the dental bleaching composition over the person's teeth for a desired treatment period, wherein the dental bleaching composition is able to adhere and retain the dental tray in place over the person's teeth duling the desired treatment period.

30. A method for bleaching a person's teeth as defined in claim 29, wherein the carrier includes at least one polyol and wherein the thickening agent includes at least one of fumed silica, a natural gum, a protein, a cellulosic ether, carboxypolymethylene, or pluronic.

* * * * *

UNITED STATES PATENT AND TRADEMARK OFFICE
CERTIFICATE OF CORRECTION

PATENT NO. : 6,322,774 B1
DATED : November 27, 2001
INVENTOR(S) : Steven D. Jensen and Dan E. Fischer It is certified that error appears in the above-identified patent and that said Letters Patent is hereby corrected as shown below:

Title page,
Please insert the Terminal Disclaimer

Column 2,
Line 19, change "provided" to -- provides --

Column 8,
Line 33, before "Example 2" insert

-- The ingredients were mixed together with the exception of sodium hydroxide. After the other ingredients were mixed, the sodium hydroxide was incrementally added in small amounts.
The foregoing procedure produced a dental bleaching composition wherein the bitter taste of the bleaching agent was fully disguised by the sucralose. The sucralose was found to be completely stable in the presence of the bleaching agent and contained the same amount of sucralose that was originally added after four months. The bleaching composition was sticky and viscous and was able to adhere and retain a dental tray in place against a person's teeth. The dental bleaching composition was useful in bleaching the person's teeth. --

Signed and Sealed this

Twenty-third Day of April, 2002

Attest:

JAMES E. ROGAN
Director of the United States Patent and Trademark Office

Attesting Officer